United States Patent [19]

Scheer

[11] Patent Number: 5,210,096

[45] Date of Patent: * May 11, 1993

[54] ANTIVIRAL COMPOSITIONS AND METHOD FOR THEIR USE

[75] Inventor: David I. Scheer, Guilford, Conn.

[73] Assignee: Chai-Tech Corporation, Greenvale, N.Y.

[*] Notice: The portion of the term of this patent subsequent to Sep. 17, 2008 has been disclaimed.

[21] Appl. No.: 728,896

[22] Filed: Jul. 10, 1991

Related U.S. Application Data

[63] Continuation of Ser. No. 502,294, Mar. 30, 1990, Pat. No. 5,106,841, which is a continuation-in-part of Ser. No. 279,417, Dec. 2, 1988, Pat. No. 5,049,557, which is a continuation-in-part of Ser. No. 147,713, Jan. 25, 1988, Pat. No. 4,866,054, and Ser. No. 147,714, Jan. 25, 1988, Pat. No. 4,866,053, which is a continuation-in-part of Ser. No. 862,804, May 13, 1986, abandoned.

[51] Int. Cl.$^5$ ............................................ A61K 34/295
[52] U.S. Cl. ..................................................... 514/501
[58] Field of Search ........................ 514/183, 185, 501

[56] References Cited

FOREIGN PATENT DOCUMENTS 1158279  7/1969  United Kingdom .

OTHER PUBLICATIONS

Bull. Chem. Soc. Jpn., (1983), 56:95-98, Kashunga et al.

*Primary Examiner*—Frederick E. Waddell
*Assistant Examiner*—Zohreh A. Fay
*Attorney, Agent, or Firm*—McAulay Fisher Nissen Goldberg & Kiel

[57] ABSTRACT

Compositions having significant activity as antiviral agent are disclosed containing, as an active component, a compound having the structural formula:

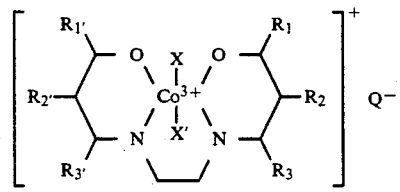

wherein $R_1$ and $R_{1'}$ are the same or different and each is an alkyl group, a phenyl group or a substituted derivative of a phenyl group;

wherein $R_2$ and $R_{2'}$ are the same or different and each is hydrogen, an unbranched alkyl group, a halide or a group having the structure $$R-\underset{\underset{O}{\|}}{C}-$$

wherein R is hydrogen, an alkoxide group, an alkyl group, or OH;

wherein $R_3$ and $R_{3'}$ are the same or different and each is hydrogen or an alkyl group;

wherein X and X' are the same or different and each is a water soluble group having weak to intermediate ligand field strength; and $Q^-$ is a soluble, pharmaceutically acceptable negative ion.

Methods of use of the inventive compositions are also disclosed.

34 Claims, 7 Drawing Sheets

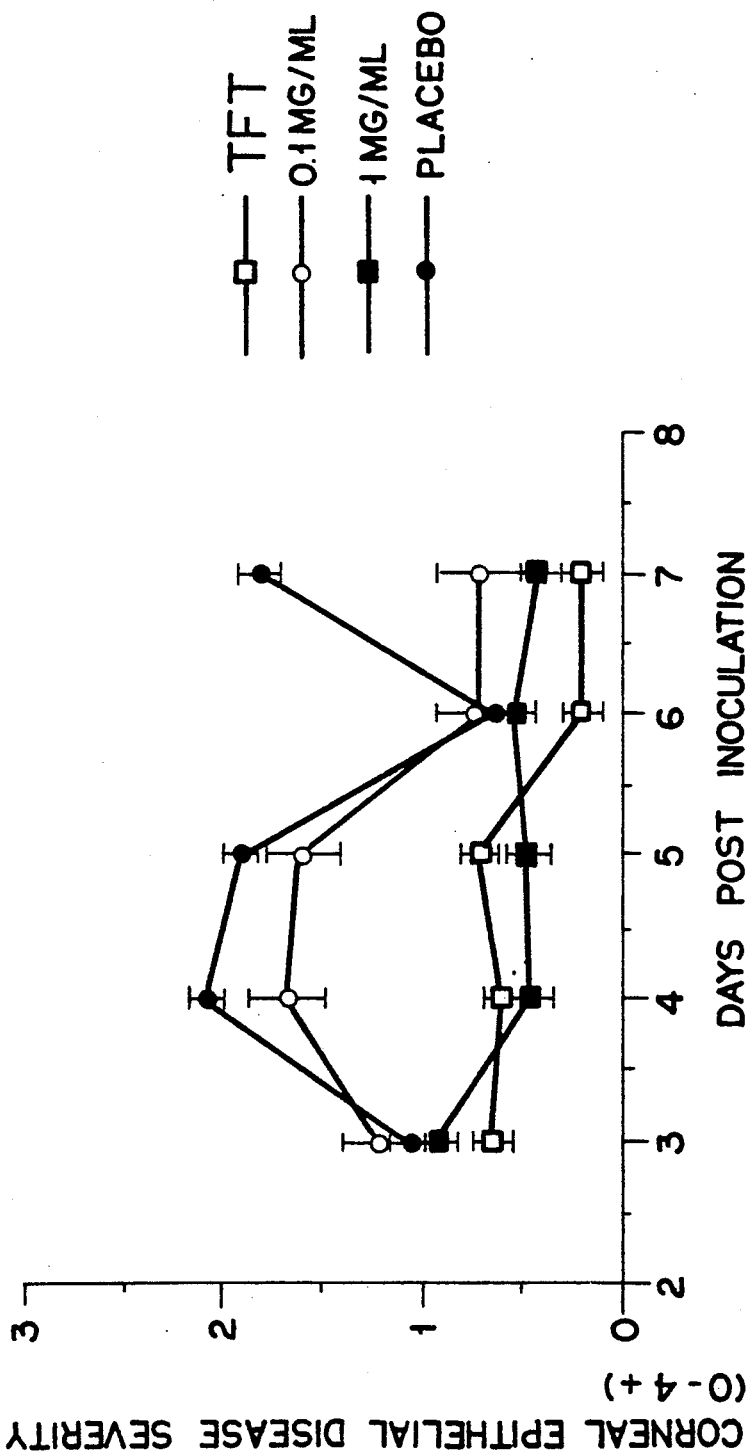
FIG. 2 CORNEAL EPITHELIAL DISEASE SEVERITY SCORES DURING CMP. 23, TFT AND PLACEBO THERAPY

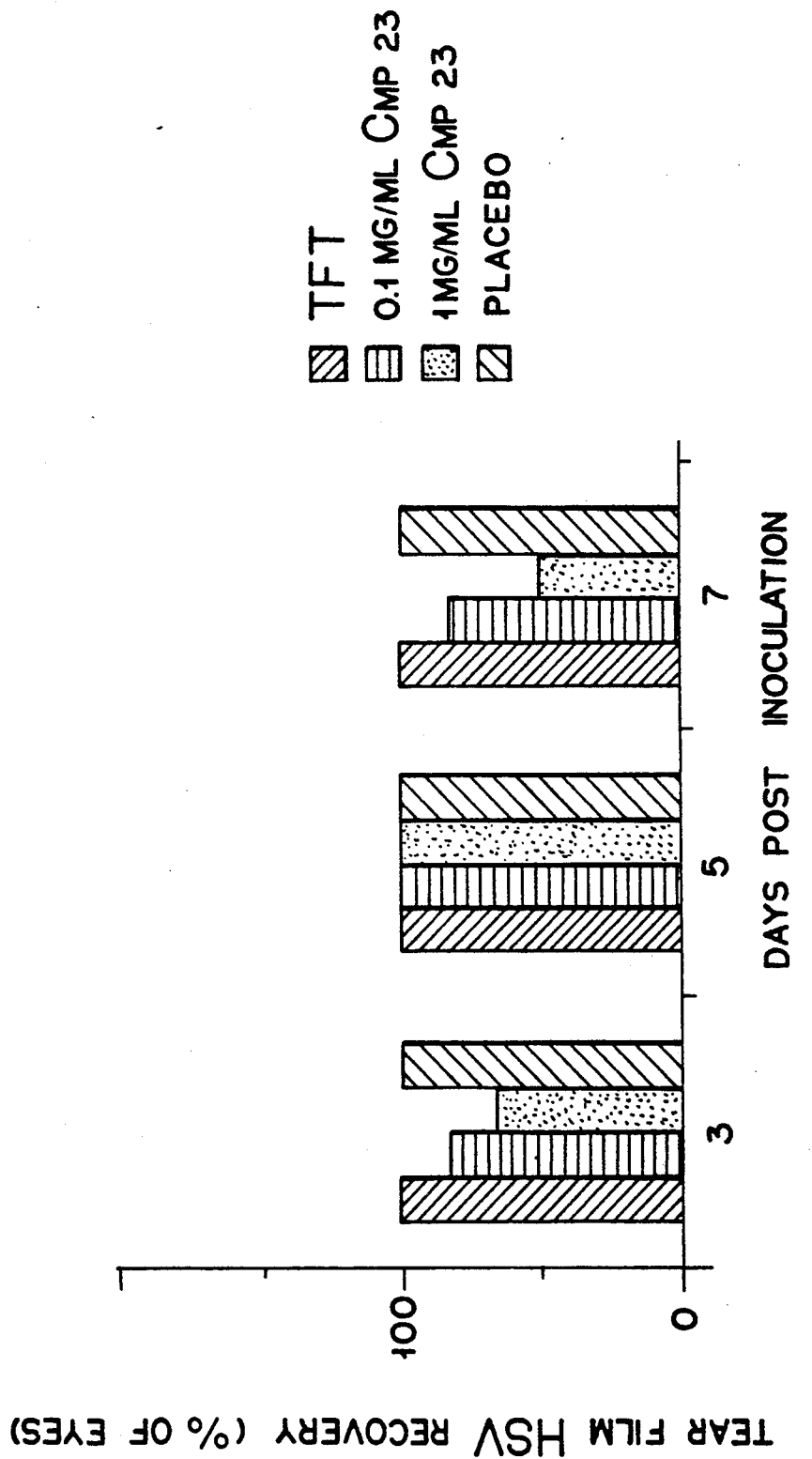
FIG. 3  TEAR FILM HSV RECOVERY ON DAYS 3, 5, AND 7 POST INOCULATION. (THERAPY WAS BEGUN ON DAY 3 POST INOCULATION.)

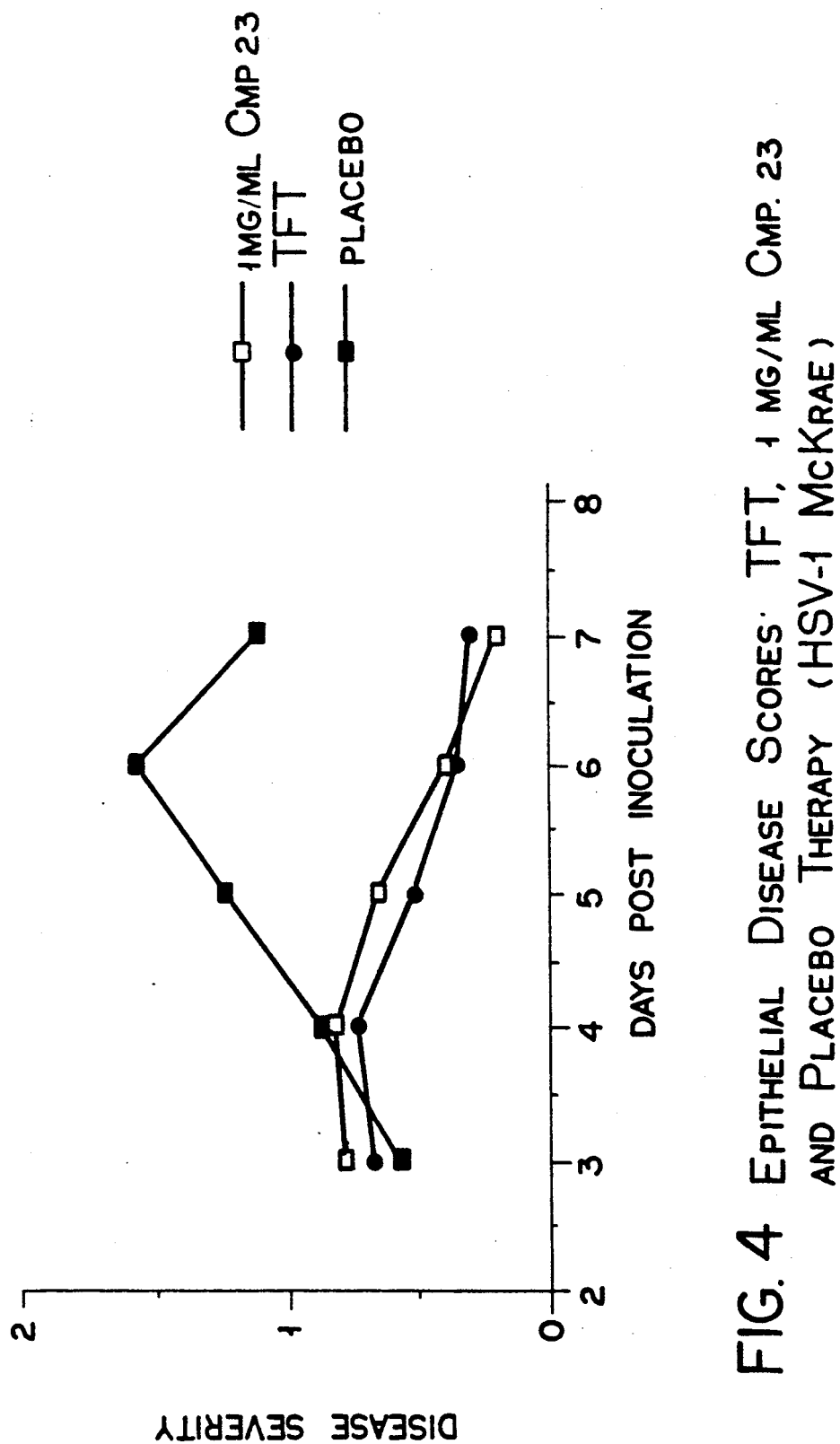
FIG. 4 EPITHELIAL DISEASE SCORES: TFT, 1 MG/ML CMP. 23 AND PLACEBO THERAPY (HSV-1 MCKRAE)

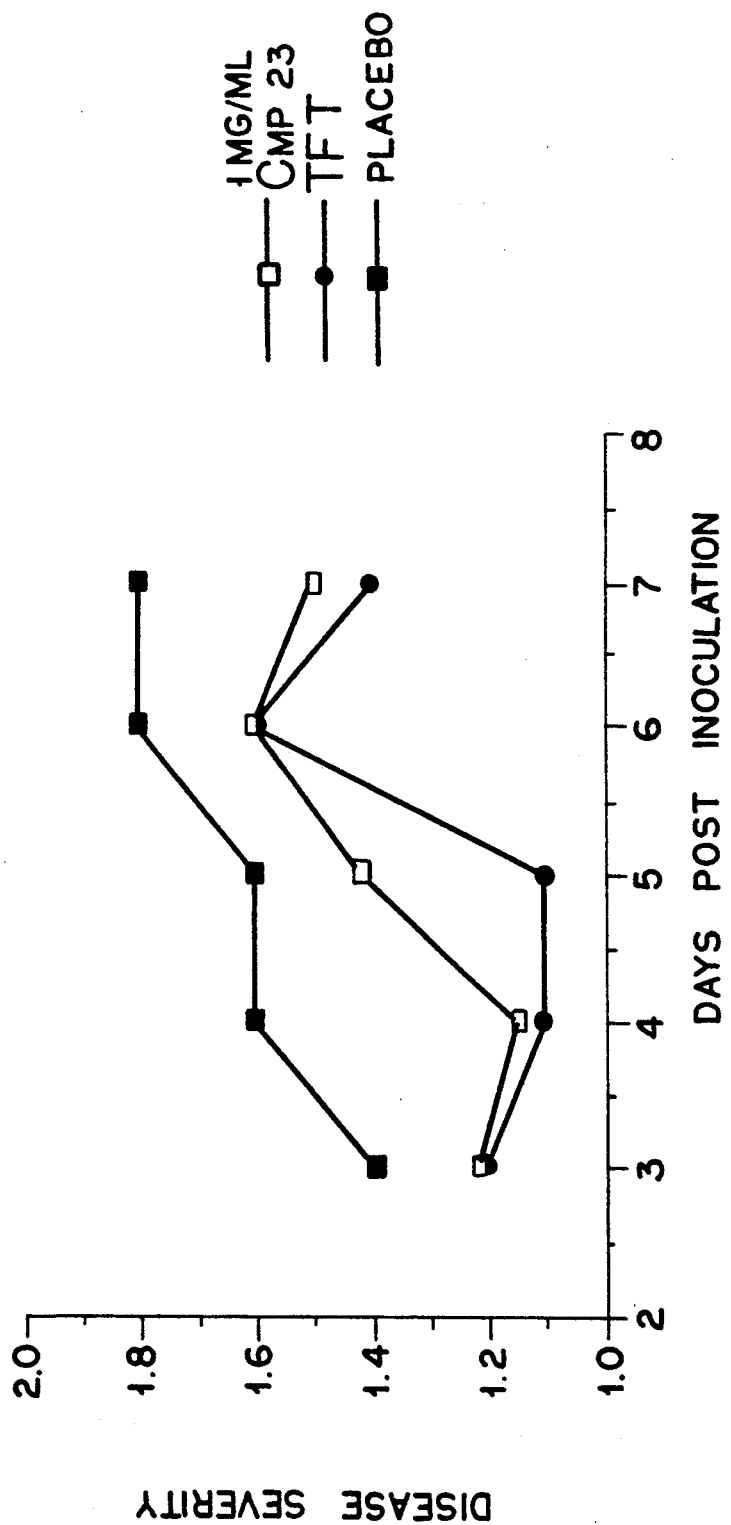
FIG. 5 EPITHELIAL DISEASE SEVERITY IN TFT, 1 MG/ML AND PLACEBO TREATED STROMAL DISEASE

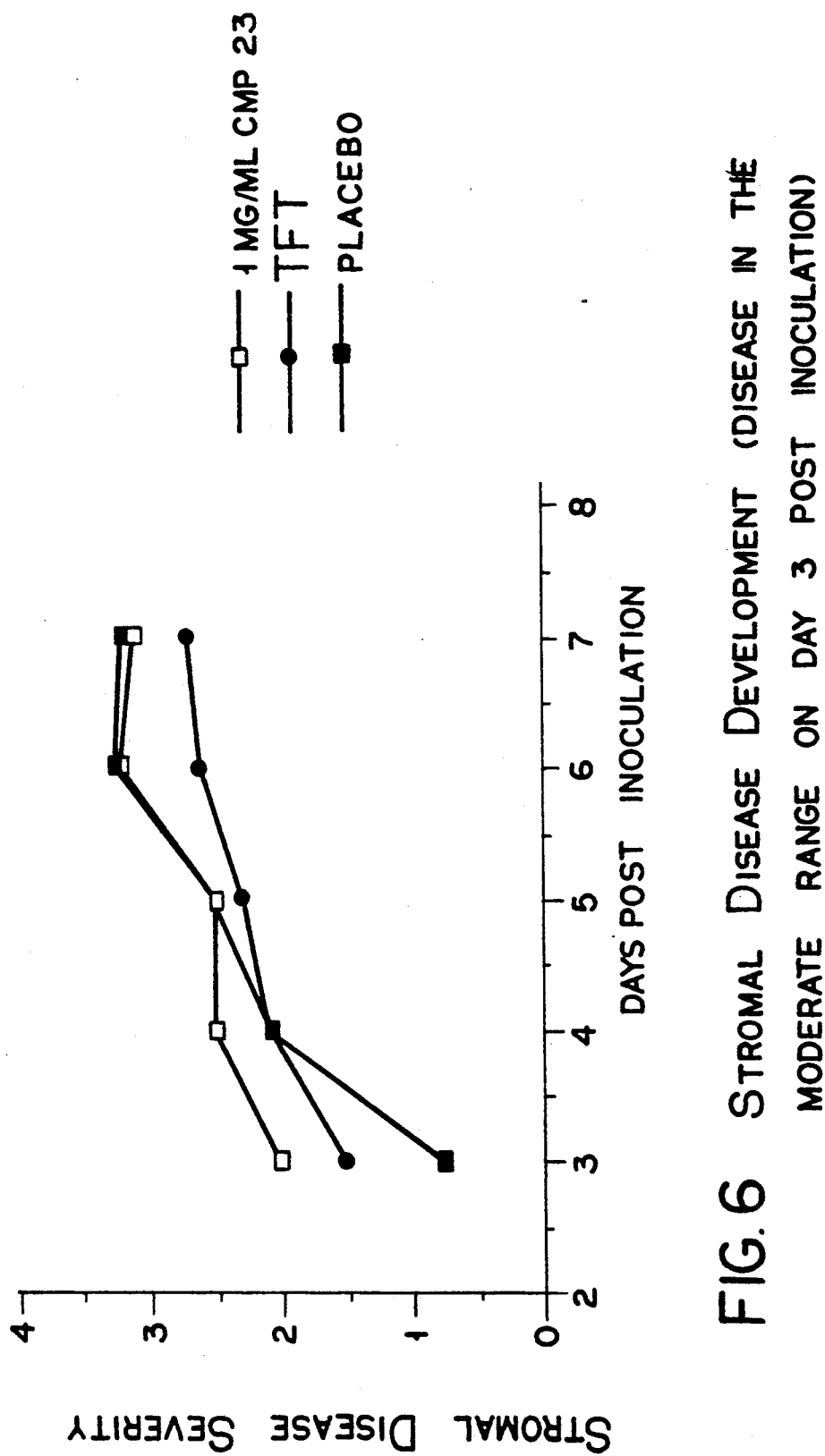
FIG. 6 STROMAL DISEASE DEVELOPMENT (DISEASE IN THE MODERATE RANGE ON DAY 3 POST INOCULATION)

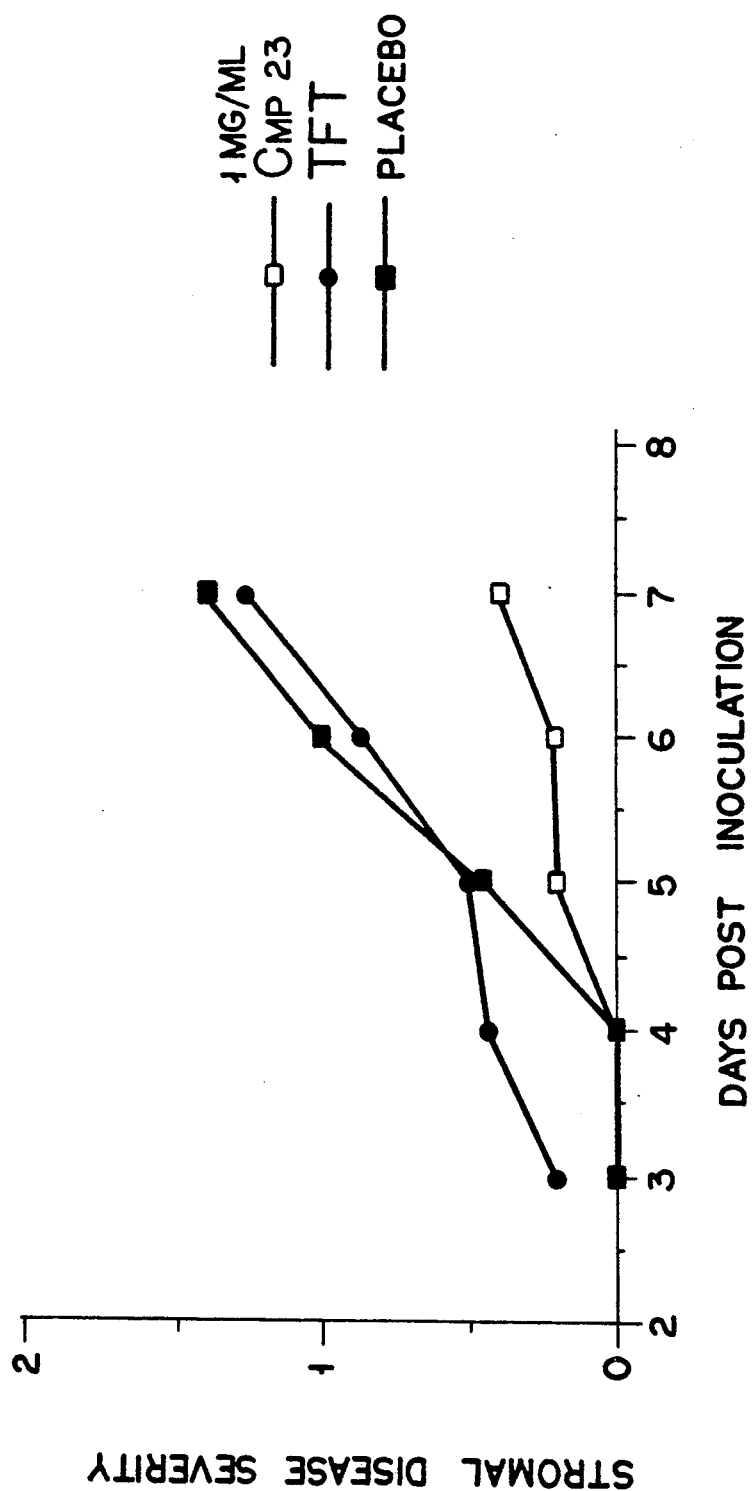
FIG. 7 STROMAL DISEASE DEVELOPMENT (MILD STROMAL DISEASE ON DAY 3 POST INOCULATION)

ANTIVIRAL COMPOSITIONS AND METHOD FOR THEIR USE

CROSS-REFERENCE TO RELATED APPLICATIONS

This is a continuation of application Ser. No. 502,294, filed Mar. 30, 1990, now U.S. Pat. No. 5,106,841 which is a continuation-in-part of U.S. application Ser. No. 07/279,417, filed on Dec. 2, 1988 now U.S. Pat. No. 5,049,557, which, in turn, is a continuation-in-part of U.S. application Ser. No. 07/147,713 and U.S. application Ser. No. 07/147,714, both filed on Jan. 25, 1988 now U.S. Pat. Nos. 4,866,054 and 4,866,053, which, in turn, are continuation-in-parts of U.S. application Ser. No. 06/862,804, filed on May 13, 1986, now abandoned. The contents of U.S. application Ser. Nos. 07/279,417, 07/147,713, 07/147,714, and 06/862,804 are hereby incorporated by reference into the present disclosure.

BACKGROUND OF THE INVENTION

The present invention relates to metallo-organic cobalt compounds and their use in the treatment of subjects for conditions and diseases caused by viruses and viral infections. It has been discovered that certain conditions and diseases, e.g., inflammation, burns, wounds, and diseases caused by bacteria and fungi in mammalian species can be treated with certain complexes of cobalt having the structure:

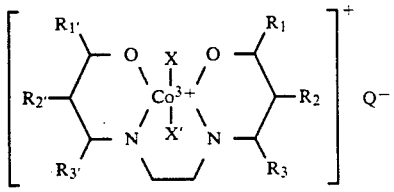

I wherein $R_1$ and $R_{1'}$ are the same or different and each is an alkyl group, a phenyl group or a substituted derivative of a phenyl group;

wherein $R_2$ and $R_{2'}$ are the same or different and each is hydrogen, an unbranched alkyl group, a halide or a group having the structure

wherein R is hydrogen, an alkoxide group, an alkyl group, or OH;

wherein $R_3$ and $R_{3'}$ are the same or different and each is hydrogen or an alkyl group;

wherein X and X' are the same or different and each is a water soluble group having weak to intermediate ligand field strength; and $Q^-$ is a soluble, pharmaceutically acceptable negative ion.

To date, however, such uses have been the only ones disclosed for these complexes.

Today, virus infections are known to be significant causes of morbidity and mortality in human and veterinary medicine. Many of these diseases are untreatable or the available therapies are not entirely satisfactory and only provide minimal clinical response. For the most part, it is known that viral diseases do not respond to therapy with conventional antibiotics. Despite some recent successes in the development of antiviral chemotherapeutic agents, new treatments for these diseases are needed to improve the management of viral infections in clinical medicine.

SUMMARY OF THE INVENTION

I have discovered that compounds having the structure of Formula I exhibit significant activity as antiviral agents. In addition, I have discovered that the compounds exhibit significant activity in comparison with known licensed antiviral agents. The compounds can be used for treating viral infections as is, or in a composition form when combined with a pharmaceutically acceptable carrier. Depending on the nature of the infection and the manner in which it manifests itself, the inventive antiviral compositions may be administered by using conventional modes of administration, e.g., oral, topical application, parenteral, and the like. The antiviral composition of the invention comprises a suitable pharmaceutically acceptable carrier and the inventive compound in an amount effective to suppress the replication and/or abort the infective life cycle of the virus causing the infection.

BRIEF DESCRIPTION OF THE DRAWINGS

FIG. 2 is a graph depicting the severity of corneal epithelial disease in animals treated with the inventive compositions and comparison compositions.

FIG. 3 is a bar graph depicting HSV-1 recovery from the tear film of animals treated with the inventive compositions and comparison compositions.

FIG. 4 is a graph similar to FIG. 2 depicting the severity of epithelial disease.

FIG. 5 is a graph depicting variations in keratitis scores with treatment time.

FIG. 6 and FIG. 7 are graphs depicting corneal stromal disease studies.

DETAILED DESCRIPTION OF THE INVENTION

Figure 1:
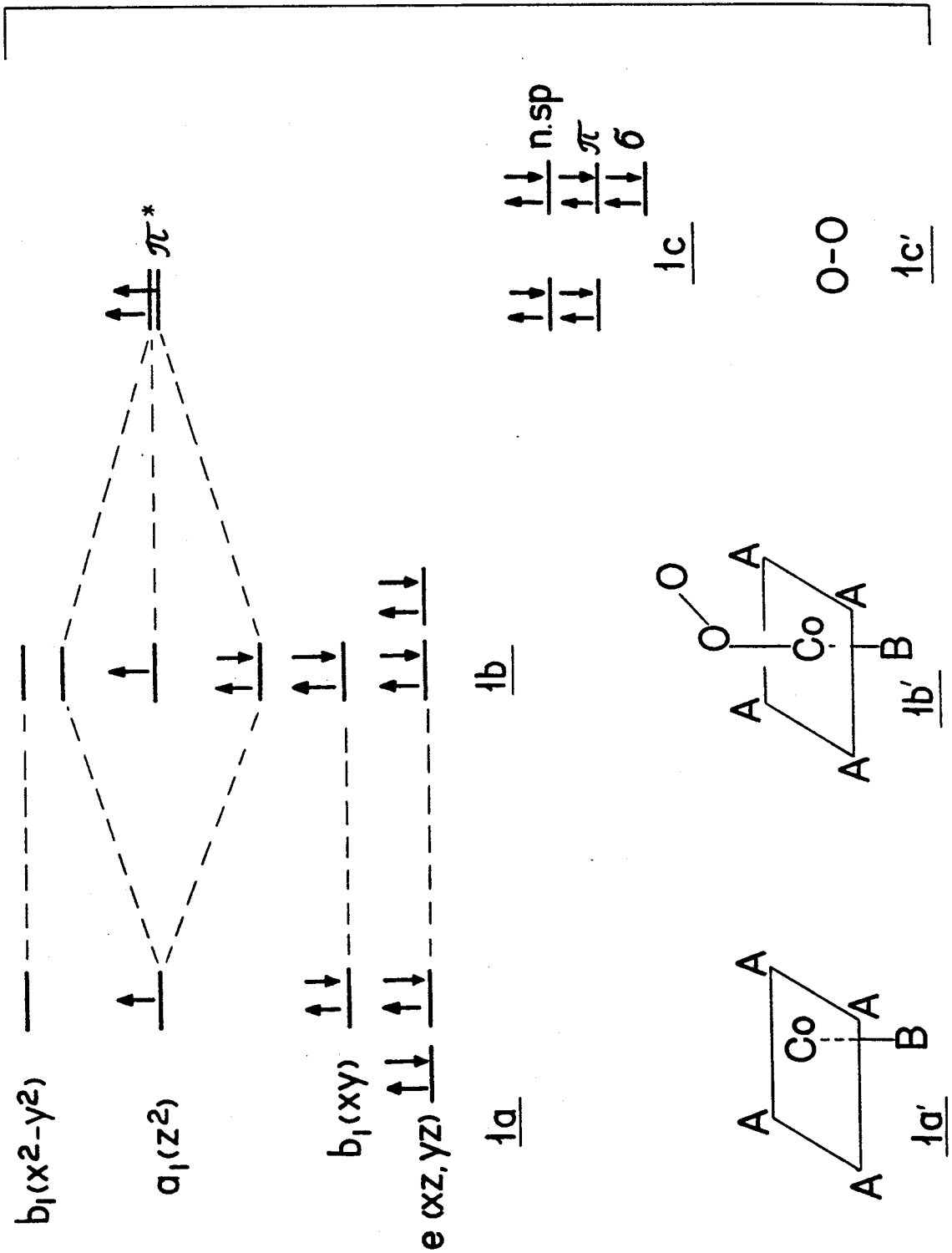
FIGS. 1a, 1a', 1b, 1b', 1c and 1c' are electron orbital and structural diagrams of compounds used in the inventive composition.

The compounds utilized in the composition of the present invention may be crystallized with numerous counteranions. Those which are pharmaceutically acceptable and are water soluble, such as, halide ions, $PF_6^-$, $BF_4^-$ and acetate are preferred.

As discussed above, the $R_1$ and $R_{1'}$ groups of the compound may be the same or different from each other and each may be an alkyl group, a phenyl group or a substituted derivative of a phenyl group. Preferably, the alkyl group is a $C_1-C_5$ group with methyl, ethyl, and butyl groups being particularly preferred. Suitable substituted derivatives of the phenyl group are derivatives wherein each substituent is a halide, an alkyl group or a group having the structure

where R is hydrogen, an alkoxide group, an alkyl group or an OH group. To date, the most useful derivatives have proven to be those in which the substituents are halides, carbonyl groups, or alkyl groups.

The $R_2$ and $R_{2'}$ groups of the complex compounds of the present invention may also be the same or different and may be hydrogen, an unbranched alkyl group, a halide or a group having the structure

where R is hydrogen, an alkoxide group, an alkyl group, or an OH group. In certain embodiments, it is preferred that $R_2$ and $R_{2'}$ are chlorine or hydrogen atoms or a $C_1$-$C_3$ alkyl group. In embodiments where $R_2$ has a structure

it is preferred that R is hydrogen, a methyl group, or an OH group.

The $R_3$ and $R_{3'}$ of the same complex compounds of the present invention are the same or different and each may be hydrogen or an alkyl group, preferably a $C_1$-$C_3$ alkyl group.

With respect to the X and X' groups, it is preferred that these groups are water-soluble and have a weak to intermediate ligand field strength. Ligands are arranged in a spectrochemical series according to the magnitude of their field strength or the "$\Delta_0$" they bring about. The symbol $\Delta_0$ represents the difference between the energies of the $d_{xy}$, $d_{xz}$, and $d_{yz}$ orbitals and the $d_z^2$ and $d_{x^2-y^2}$ orbitals in octahedral complexes. From experimental studies, it is known that the order of ligands, based on their ligand field strength is approximately the same for the complexes of all the transition metals in their common oxidation states with only an occasional inversion of order between ligands that stand near to one another. A typical order of some common ligands is as follows:

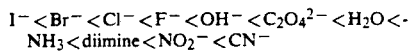

The cyanide ion, which stands at the opposite end of the series from the halide ions, has a strong ligand field strength and induces the largest d-orbital splitting of any ligand listed. On the other hand, the halide ions, such as, $Br^-$ and $Cl^-$ have weak ligand field strength and induces the smallest d-orbital splitting. Ligands, such as, $NH_3$ and $OH^-$ have intermediate ligand field strength. For general background information, see F. Albert Cotton and Geoffrey Wilkinson, *Advanced Inorganic Chemistry*, John Wiley & Sons, 4th ed., p. 663. In the present invention, it is preferred that X and X' are ligands with weak to intermediate ligand field strength, such as, halides or $NH_3$, $H_2O$, or dimethyl sulfoxide or any ligand in the spectrochemical series having a ligand field strength less than $CN^-$. Particularly preferred embodiments of the complex compounds are as follows:

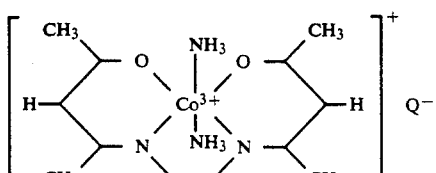

Compound No. 23

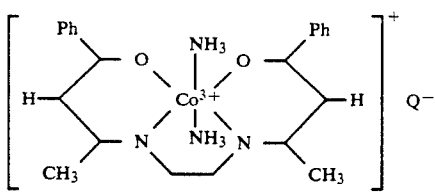

Compound No. 64

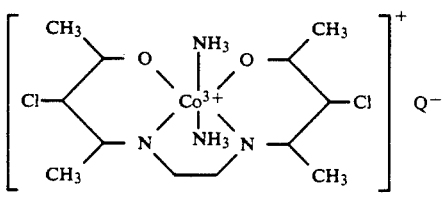

Compound No. 67

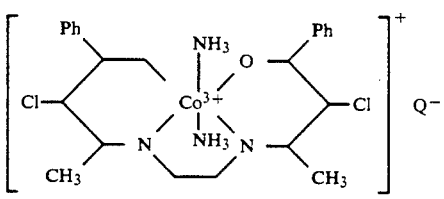

Compound No. 68

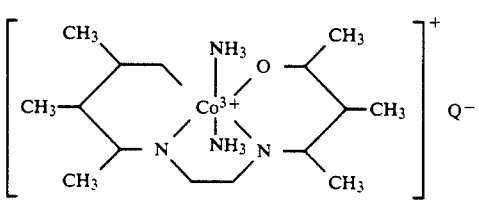

Compound No. 69

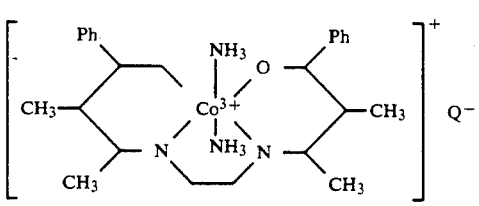

Compound No. 70 wherein Ph is a phenyl group.

The inventive composition comprises a pharmaceutically acceptable carrier and the compound as defined above in an antivirally effective amount. It is understood, of course, that generally, in the treatment of conditions which result from viral infections, a dosage regimen is required in which the medication is provided over a period of time.

The inventive composition exhibits activity against viruses which are resistant to known antiviral agents presently being sold for therapeutic use against such viruses. Normally, such an agent, in order to sold, must be licensed by a regulatory authority of the country in which it is being sold. As used herein, the expression "existing licensed antiviral agent" means an agent (compound or composition) which is currently licensed for sale and/or use in antiviral therapy.

In any event, in treatments using the inventive compositions, it is important that an antivirally effective dosage regimen be used. As used herein, the expression anti-virally effective amount or dosage or regimen means that amount, dosage or regimen which results in sufficient concentrations of the particular compound at the cellular sites of infection which are sufficiently in excess of those concentrations necessary to inhibit virus replication and/or abort the virus's infective life cycle. In the examples set forth hereinafter, median inhibitory concentrations ($MIC_{50}$) are depicted which are concentrations of a drug necessary to inhibit 50% of the replication of the virus.

The inventive composition may be administered orally, in suitable dosage forms, for example, dragees, capsules, tablets, elixirs, or other oral dosage forms. Also, the composition can be administered parenterally, e.g., in sterile distilled water or physiological saline. For topical administration, the inventive composition may be placed in dimethyl sulfoxide (DMSO) or in the form of ointments, salves, creams, and the like.

Typically, the dosage may be administered 1 to 9 times daily, depending upon the severity and nature of the viral condition or on a schedule less frequent than daily, e.g., every other day, weekly, and the like. The inventive composition may be formulated in a sustained release or controlled release system such as that consisting of a micro-encapsulated form, or through other systems such as encapsulation within liposomes. These sustained release systems can permit less frequent dosing while achieving the desired therapeutic efficacy. Preferably, the administration is under medical supervision so that the dosage may be reduced or the number of daily administrations limited as the viral infection subsides.

The compounds of the present invention are water soluble and may be dissolved in a number of carriers. Suitable carriers include polar, protic solvents, such as, water, or normal saline. The compounds may also be suspended in a suspension medium that is not miscible with water, for example, petrolatum, or in an amphiphatic solvent, such as; DMSO.

When these inventive compositions are to be administered by the topical route, the concentration in the solvent suspension medium can vary from 0.1 to 50 mg/ml. A preferred concentration range lies between 0.5 and 10 mg/ml.

When the inventive compositions are to be given by parenteral or oral routes, a dosage range of 0.01 mg/kg/day to 100 mg/kg/day can be used.

The synthesis of the compounds of the present invention are described in U.S. application Ser. No. 07/279,417, referred to and incorporated by reference hereinabove. As noted therein, the reaction of Co(II) complexes with molecular oxygen has been studied extensively (see, R. S. Drago and B. R. Corden, Acc. Chem. Res., 1980, 13, 353 & E. C. Niederhoffer, J. H. Timmons and A. E. Martell, Chem. Rev. 1984, 84, 137). Normally, cobalt (II) forms 2:1 peroxo bridged complexes in aqueous solutions (see, E. C. Niederhoffer, J. H. Timmons and A. E. Martell, Chem. Rev. 1984, 84, 137). In recent years, a number of Co(II) complexes have been reported to give 1:1 cobalt-oxygen adducts at room temperature. These complexes usually contain ligands which when bound to Co(II) give rise to a low spin planar geometry. Addition of base and $O_2$ to these complexes leads to the formation of octahedral complexes where the base and the $O_2$ occupy axial positions (see, A. Summerville, R. D. Jones, B. M. Hoffman and F. Basolo, J. Chem. Educ., 1979, 56, 3, 157).

On the basis of measurements utilizing a variety of physical techniques it is now a well-accepted fact that the most accurate electronic structure description of the $Co:O_2$ moiety is a Co(III) ion bound to $O_2$, where the actual amount of Co→$O_2$ electron transfer depends on the nature of the ligand and the donor set (see, A. Summerville, R. D. Jones, B. M. Hoffman and F. Basolo, J. Chem. Educ., 1979, 56, 3, 157, & D. Getz, E. Melamud, B. L. Silver and Z. Dori, J. Am. Chem. Soc., 1975, 97, 3846). It has been shown that electron transfer increases with increase of the ligand field strength (see, R. S. Drago and B. R. Corden, Acc. Chem. Res., 1980, 13, 353). This can be easily understood from the molecular orbital diagram depicted in FIG. 1.

FIGS. 1a, 1a', 1b, 1b', 1c and 1c', which comprise, in their totality, FIG. 1, are to be read together. Each of FIG. 1a represents the electron molecular orbital diagram of each of the moieties shown directly below it. Thus, FIG. 1a is the molecular orbital diagram for the complex prior to having the $O_2$ adduct thereon, which is depicted as FIG. 1a'. FIG. 1b is the molecular orbital diagram of the complex depicted in FIG. 1b' with the oxygen adduct thereon. FIG. 1c is the diagram of diatomic $O_2^-$. $O_2^-$ is shown in FIG. 1c'.

In FIGS. 1a' and 1b', the donor atoms A define the basal plane of the molecule, while B represents the axial ligands. As the ligand field strength of the donor atoms around the cobalt increases, the metal orbitals (especially $d_z^2$ and $d_{x^2-y^2}$ which are $\sigma$ orbitals) are raised in energy relative to the $\pi^*$ orbitals of $O_2$ and more electronic charge is transferred from the metal to the bound dioxygen, i.e., the $O_2$ molecule attains more $O_2^-$ character. Thus, considering electronic structural arguments only, one can conclude that a Co(III) complex with a set of six donor atoms (four A donors, and two B donors) having an intermediate ligand field strength could be effective in reacting with $O_2^-$ by either forming a stable Co(III)-$O_2$ adduct (the $O_2$ substitutes one of the B ligands), or by oxidizing $O_2^-$, liberating dioxygen and yielding a Co(II) complex. The relative strength of the different ligands is well-known from the spectrochemical series. However, it should be quite clear that a sterically unstrained ligand system which can easily accommodate both metal oxidation states [Co(II), Co(III)] with minimal reorganization of the geometry around the metal and which does not lead to a high spin Co(II) complex should facilitate the reaction.

Thus, on the basis of geometrical, steric and electronic requirements, we suggest that a Co(III) complex having a quadridentate ligand which imposes planarity on the octahedral basal plane should be a suitable candidate for reaction with the $O_2^-$ radical anion. The effectiveness of this reaction will depend on the nature of the quadridentate ligand, its ligand field strength and on the nature of the axial ligands B.

The complexes [CoL(NH$_3$)$_2$]$^+$ fit nicely with the set of requirements given above. First, the six donor atoms $N_4O_2$ give rise to an intermediate ligand field. Secondly, the quadridentate ligand L when bound to Co(III) gives rise to a 6,5,6 ring system where the six membered rings are unsaturated, thereby ensuring the planarity of the complex basal plane without steric strain, as has been determined from X-ray crystal structure analysis. Thirdly, the ligand L when bound to Co(II), gives a low spin, planar complex.

It should be pointed out that the unsaturation of the six-membered rings is important not only because it ensures the required geometry, but also because it provides for an effective pathway for transmitting electronic effects of different substituents to the cobalt center, thereby affecting the relative energies of the metal d orbitals.

The following examples illustrate the present invention:

In the examples, the methods used were as outlined in the references cited:

1. For in vitro antiviral activity testing in a modified Vero cell culture model (Example 3) and the determination of virus titers in tear film samples (Examples 1 and 2), see Green and Dunkel, *Antimicrob Agents and Chemother* 20; 580–582, 1981; and Trousdale, Dunkel and Nesburn, *Invest. Ophthalmol. Vis. Sci.* 19; 1336–1341, 1981.

2. For in vivo epithelial HSV-1 induced keratitis (Examples 1 and 2), see Trousdale, Dunkel, Nesburn, *Invest. Ophthalmol. Vis. Sci.* 19; 267–270, 1980; Pavan-Langston, Lass, Campbell, *Am. J. Ophthalmol.* 86; 618–623, 1978; Green, Dunkel, Pavan-Langston, *Exp. Eye Res.* 45; 375–387, 1987.

3. For vivo corneal stromal HSV-1 induced keratitis, see Sabbaga, Pavan-Langston, Bean, Dunkel, *Exp. Eye Res.* 47; 545–553; Boisjoly, Woog, Pavan-Langston, Park, *Arch. Ophthalmol.* 102; 1804–1807, 1984; Pavan-Langston, Dunkel, *Arch. Ophthalmol.* 107; 1068–1072, 1989.

EXAMPLE 1

Twenty NZW rabbits were examined to determined the presence of pre-existing corneal defects by slit lamp examination after installation of fluorescein. All animals were then bilaterally inoculated with $10^5$ PFU of McKrae strain HSV-1. On day 2 post inoculation, rabbit #5 expired. On day 3 post-inoculation, the eyes of the remaining animals were examined and graded by slit lamp biomicroscopy. Nine of the 19 animals had acceptable disease severity for treatment. These nine animals were divided into treatment groups as follows:

2 animals were treated with 5-(trifluoromethyl)-2'deoxyuridine (TFT) (an existing licensed antiviral agent)
3 animals were treated with 0.1 mg/ml of Compound #23
3 animals were treated with 1 mg/ml of Compound #23
1 animal was treated with a placebo Treatment was begun on day 3 post-inoculation, with applications of one drop of solution (40 ml) nine times per day. Tear film virus recovery for each animal was performed on day 1 (preculture), and post-inoculation days 3, 5, and 7.

Of the remaining 10 animals, ocular disease severity was sufficient on day 4 post-inoculation and treatment was begun. These animals were treated with applications nine times per day as follows:
TFT: 3 animals
0.1 mg/ml of Compound #23: 3 animals
1 mg/ml of Compound #23: 3 animals
Placebo: 1 animal Tear film virus recovery for each animal was performed on these animals on day 1 prior to inoculation and post-inoculation days 3, 4, 5, and 7.

FIG. 2 depicts the corneal epithelial severity (keratitis) scores for treatment with each of the medications for various periods post-inoculation. As shown, in those animals treated with TFT, peak disease occurred on day 5 post-inoculation (average keratitis score equal to about 0.7). By day 7 post-inoculation, ocular disease had decreased to a 0.2 level. HSV was recovered in all TFT-treated eyes on days 3, 5, and 7 post-inoculation.

FIG. 3 is a bar chart showing the recovery of HSV in tear film on days 3, 5, and 7 post-inoculation. (Treatment was begun on the third day after inoculation.)

The titer of virus recovered from the tear films ranged from $10^2$ to $10^3$ PFU/ml. Mild ocular toxicity was evident in the TFT treated eyes on days 5 through 7 post-inoculation as fluorescein pooling, corneal pitting and thinning, and persistent focal superficial punctate keratitis.

On days 5 and 7 post-inoculation, a mild stromal haze and stromal edema was observed in two out of the four TFT treated eyes. It is noted that the development of stromal HSV-induced disease after primary topical infection is variable and generally occurs between 5 and 15 days post-inoculation. 15 to 60% of topically inoculated eyes will develop mild stromal complications and stromal disease will resolve by 20 to 25 days after inoculation. These animals were at the initial stage of the stromal disease development at this time.

Those animals treated with 0.1 mg/ml of Compound 23 exhibited peak corneal epithelial disease on day 4 post-inoculation. The ocular disease began to resolve on day 7 post-inoculation. As can be seen from FIG. 2, the efficacy curve for therapy with 0.1 mg/ml is similar to that observed with the placebo. While there does not appear to be a statistically significant difference between the 0.1 mg/ml of Compound 23 therapy and placebo therapy on days 3, 4, 5, and 6 post-inoculation, a statistically significant difference was observed with 1 mg/ml of Compound 23 and TFT on days 4, 5, and 7 post-inoculation ($p < 0.01$).

A statistically significant improvement was observed for the 0.1 mg/ml treatment with Compound 23 relative to that observed with the placebo on day 7 ($p < 0.01$).

Referring to FIG. 3, tear film HSV recovery for the 0.1 mg/ml group was 83% on day 3 post-inoculation and 83% on day 7 post-inoculation indicating that this concentration, administered according to this treatment regimen, does not represent an antivirally effective amount. Virus titers in the tear film cultures ranged from about $10^2$ to $10^3$ PFU/ml and stromal disease was not evident in any of the animals treated with 0.1 mg/ml of Compound 23.

For those animals treated with 1.0 mg/ml of Compound 23, peak corneal epithelial disease occurred on the third day post-inoculation which was the day on which treatment was initiated. Within one day of therapy, the average HSV-induced keratitis score had decreased by almost 50% for this group. The keratitis severity within this group exhibited a rate of decrease greater than that for the TFT-treated animals and the scores continued to decrease throughout the study. Overall, the therapeutic efficacy curve for therapy with 1.0 mg/ml of Compound 23 was similar to that for TF. Stromal disease was not evident in the animals treated with the 1.0 mg/ml of Compound 23 and tear film recovery of HSV was 66% on day 3 post-inoculation and 50% on day 7 post-inoculation. The value of 100% recovery on day 5 post-inoculation is attributed to experimental error. Tear film titers for the virus ranged from $10^2$ to $10^3$ PFU/ml.

For the placebo treated animals, ocular disease peaked on days 4-5 post-inoculation. By day 7 post-inoculation, the ocular disease was resolving. HSV virus was recovered from all tear film cultures on days 3, 5, and 7 post-inoculation. Titers ranged from $10^3$ to 10⁴ PFU/ml and mild stromal disease was evident in one of the two placebo-treated eyes.

For those animals treated with 0.1 and 1.0 mg/ml of Compound 23 on day 4 post-inoculation, topical therapy was not effective.[1]

[1] As can be seen from FIG. 2, the disease severity with the placebo therapy at day 6 post-inoculation decreased drastically and then rose to the previous observed levels observed on day 7 post-inoculation. This is believed to be an experimental abnormality. Additionally, it is considered that the initiation of antiviral therapy beginning on day 4 after inoculation is not clinically valid because: (1) the therapy was begun too late to arrest the HSV ocular complications (including both epithelial and superficial stromal), and (2) the analysis of the efficacy became complicated due to the variability in the range of the clinically observable corneal epithelial disease as well as the area of the cornea that is involved in overt and pre-clinical disease.

EXAMPLE 2

Fifteen NZW rabbits were initially examined using a slit lamp after instillation of fluorescein to ascertain the presence of any pre-existing corneal defects. All the animals were then bilaterally inoculated with 10⁵ PFU of the McKrae strain of HSV-1. On day 3 post-inoculation, the eyes of all of the animals were examined and graded by slit lamp biomicroscopy. Therapy was begun on the third day after inoculation. The animals were treated in the same manner as in Example 1. Thus, five animals were treated with Compound 23 at a concentration of 1 mg/ml. Five animals were treated with 1% trifluorothymidine and five animals with placebo therapy. The treatment was continued for seven days, during which time the animals were observed by slit lamp examination daily to document the efficacy of Compound 23 and TFT. Tear film cultures were performed on days 3, 5, and 7 post-inoculation to evaluate the titers of HSV remaining in the tear film.

The results were similar to those observed in Example 1 and confirmed the effectiveness of Compound 23 in reducing the development of HSV-1 ocular disease in the rabbit model. The reduction of HSV-1 disease by Compound 23 therapy was comparable to that observed with TFT therapy. However, Compound 23 exhibited superior overall therapeutic results as compared to TFT therapy with respect to the absence of stromal disease development as well as the lack of corneal epithelial cell toxicity.

FIG. 4 depicts the severity of epithelial disease observed in this study. It indicates that the results with Compound 23 are comparable to those observed with TFT. At day 5, the difference in disease severity between TFT- and Compound 23-treated eyes appears to be significant. Certainly, the overall response to therapy appears to be comparable for both compounds.

In particular, peak disease in the TFT-treated animals occurred on days 4-5 post-inoculation with an average keratitis score equal to 0.87. By the seventh day post-inoculation, the ocular disease had decreased to a 0.1-0.2 level. HSV was recovered from all TFT-treated eyes on day 3 post-inoculation. Specifically, on day 3, virus was recovered from 40% of the TFT-treated eyes. On day 7 post-inoculation, virus was recovered from 20% of the TFT-treated eyes. Mild toxicity was evident in the TFT-treated eyes on days 5 through 7 post-inoculation. (The toxicity level was manifested as the development of a mild superficial punctate keratitis and mild to moderate fluorescein pooling on the epithelial surface.) On days 6-7 post-inoculation, a mild stromal haze was observed in 2 out of the 10 TFT-treated eyes. (It is noted that the development of stromal HSV-induced disease after primary infection usually occurs between the 5th and 15th day post-inoculation. These animals were only at the initial stages of stromal disease development.)

For the animals treated with 1.0 mg/ml of Compound 23, the disease peaked on days 3 to 4 post-inoculation. Within one day of therapy, the average HSV-induced keratitis scores had decreased by almost 40-50%. These scores continued to decrease throughout the remainder of the study. The therapeutic efficacy curve for 1.0 mg/ml of Compound 23 is similar to that for TFT. On days 3 and 4 post-inoculation, Compound 23 therapy was a good as TFT therapy. Stromal disease was not evident in the Compound 23-treated animals. Tear film HSV recovery ranged from 100% on day 3 post-inoculation to 70% on day 5 and 40% on day 7.

In the placebo-treated animals, ocular disease peaked on days 5-6 post-inoculation. By day 7, the ocular disease was resolving. Still, the disease scores on day 7 were higher than those for the TFT-and Compound 23-treated animals. HSV was recovered from all tear film cultures on days 3 and 5 post-inoculation and from 80% of the tear film cultures on day 7 post-inoculation. Mild stromal disease was evident in 4 of the 10 placebo-treated eyes on days 6 through 7 post-inoculation. These results indicate that the responses to Compound 23 were as good as those to TFT.

EXAMPLE 3

An evaluation of the in vitro efficacy of the inventive compounds during tissue culture viral infection was carried out. For this purpose, six different virus strains and four different concentrations of the inventive compounds were evaluated. Inhibition of virus production was determined. The results are shown in terms of log titer reduction of virus.

Initial inocula of 10⁴ PFU of the following viruses were used:
McKrae strain HSV-1
MS strain HSV-2
HCMV clinical isolate
VZV clinical isolate
HSV-1 (TFT resistant)
Adenovirus-Strain 19

The compounds were tested at concentrations of 0.01, 0.1, 1, and 5 mg/ml.

The virus stocks were absorbed onto confluent Vero or MRC5 cell monolayers for 30 minutes at 37° C. The inocula were aspirated and the media containing the inventive compounds at each of the given concentrations were applied to the cell monolayers. The cell monolayers were incubated at 37° C. and examined by inverted light microscopy. Viral titers were determined after 3 days of incubation.

The analysis of the plaque reduction assays for each of the inventive Compounds 23, 64, and 67, are shown in Tables 1, 2, and 3, respectively. Table 4 is a summary comparison of the efficacy of the inventive composition against the viruses which were tested. These data shown that Compound 23 at a concentration as low as 0.1 mg/ml was effective in vitro against HSV-1, HSV-2, HSV-1 (TFT-R), and Adenovirus Strain 19. The composition containing 0.01 mg/ml of Compound 64 was effective against HSV-1, HCMV, and VZV. Compound 67 at a concentration of 0.01 mg/ml was effective against HCMV, VZV, and Adenovirus. Accordingly, these data show that the inventive compositions are effective against a variety of viruses at relatively low concentrations. While certain of these compounds may not be effective against certain viruses, it is clear from these data that these same compounds can effectively inhibit other viruses against which the other compounds are not effective. Accordingly, the present invention includes the inventive compositions wherein the composition contains a compound as defined hereinabove in an amount which is effective against the specific virus being treated. Known viruses of clinical significance are disclosed in Stedman's Medical Dictionary, 24th Ed., Williams & Wilkins, pp. 1559-1565, (1982); Virology, B. N. Fields, D. M. Knipe, R. M. Chanock, J. L. Melnick, & R. E. Shope, Raven Press, N. Y. (1985).

TABLE 1

COMPOUND 23 EFFICACY IN VITRO AGAINST HSV-1, HSV-2, HSV-1 (TFT-R), HCMV, VZV and Adenovirus-19

| Compound 23 | Drug Concentration (mg/ml) | | | | |
|---|---|---|---|---|---|
| | 0.0001 | 0.001 | 0.01 | .1 | 1 |
| HSV-1 | $10^3$ | $10^{3-2}$ | $10^2$ | 0 | 0 |
| HSV-2 | $10^{2-3}$ | $10^2$ | $10^{2*}$ | $10^{0-1}$ | 0 |
| HSV-1 (TFT-R) | $10^{1*}$ | 0 | 0 | 0 | 0 |
| HCMV | $10^4$ | $10^4$ | $10^4$ | $10^3$ | $10^3$ |
| VZV | $10^4$ | $10^4$ | $10^3$ | $10^3$ | $10^3$ |
| Adenovirus-19 | $10^3$ | $10^{1-2*}$ | $10^1$ | $10^1$ | 0 |

*Indicates the concentration at which 50% reduction in plaque forming units is observed ($MIC_{50}$). $10^4$ PFU of all virus stocks were overlaid onto confluent Vero cell monolayers (HSV-1, HSV-2 and TFT-R HSV-1) or MRC5 cell monolayers (HCMV, VZV, and Adenovirus-19). Compound 23 was toxic to the cell monolayers at a concentration of 5 mg/ml.

TABLE 2

COMPOUND 64 EFFICACY IN VITRO AGAINST HSV-1, HSV-2, HSV-1 (TFT-R), HCMV, VZV and Adenovirus-19

| Compound 64 | Drug Concentration (mg/ml) | | | | |
|---|---|---|---|---|---|
| | 0.0001 | 0.001 | 0.01 | .1 | 1 |
| HSV-1 | $10^3$ | $10^{2-3}$ | $10^{2*}$ | $10^1$ | 0 |
| HSV-2 | $10^4$ | $10^4$ | $10^4$ | $10^3$ | $10^3$ |
| HSV-1 (TFT-R) | $10^4$ | $10^3$ | $10^3$ | $10^3$ | $10^{2-3*}$ |
| HCMV | $10^{2*}$ | $10^2$ | $10^2$ | $10^1$ | $10^1$ |
| VZV | $10^3$ | $10^{2*}$ | $10^2$ | $10^{1-2}$ | 0 |
| Adenovirus-19 | $10^4$ | $10^4$ | $10^4$ | $10^4$ | $10^4$ |

*Indicates the concentration at which 50% reduction in plaque forming units was observed ($MIC_{50}$). $10^4$ PFU of all virus stocks were overlaid onto confluent Vero cell monolayers (HSV-1, HSV-2 and HSV-1 (TFT-R)) or MRC5 cell monolayers (HCMV, VZV, and Adenovirus-19). Compound 64 was extremely toxic to the cell monolayers at a concentration of 5 mg/ml. In addition, Compound 64 was difficult to hydrate and did not remain in solution. The solution was more viscous than the other compounds tested.

TABLE 3

COMPOUND 67 EFFICACY IN VITRO AGAINST HSV-1, HSV-2, HSV-1 (TFT-R), HCMV, VZV and Adenovirus-19

| Compound 67 | Drug Concentration (mg/ml) | | | | |
|---|---|---|---|---|---|
| | 0.0001 | 0.001 | 0.01 | .1 | 1 |
| HSV-1 | $10^4$ | $10^4$ | $10^{2-3}$ | $10^{2*}$ | $10^2$ |
| HSV-2 | $10^4$ | $10^4$ | $10^4$ | $10^3$ | $10^{2-3*}$ |
| HSV-1 (TFT-R) | $10^4$ | $10^4$ | $10^3$ | $10^3$ | $10^{2-3*}$ |
| HCMV | $10^3$ | $10^{2-3}$ | $10^{2*}$ | $10^2$ | 0 |
| VZV | $10^3$ | $10^{2*}$ | $10^2$ | $10^1$ | 0 |
| Adeno-virus-19 | $10^3$ | $10^3$ | $10^{2*}$ | $10^1$ | $10^1$ |

*Indicates the concentration at which 50% reduction in plaque forming units was observed ($MIC_{50}$). $10^4$ PFU of all virus stocks were overlaid onto confluent Vero cell monolayers (HSV-1, HSV-2 and HSV-1 (TFT-R)) or MRC5 cell monolayers (HCMV, VZV, and Adenovirus-19). Compound 67 was extremely toxic to the cell monolayers at a concentration of 5 mg/ml. Compound 67 was moderately toxic to the cell monolayers at a concentration of 1 mg/ml.

TABLE 4

COMPARATIVE ANTIVIRAL EFFICACY OF INVENTIVE COMPOSITIONS ($MIC_{50}$ in terms of mg/ml)

| | Compound 23 | Compound 64 | Compound 67 |
|---|---|---|---|
| HSV-1 | 0.01 | 0.01 | 0.1 |
| HSV-2 | 0.01 | >1 | >1 |
| HSV-1 (TFT-R) | <0.0001 | >1 | >1 |
| HCMV | >1 | 0.0001 | 0.01 |
| VZV | >1 | 0.001 | 0.001 |
| Adenovirus-19 | 0.001 | >1 | 0.01 |

EXAMPLE 4

A study was carried out to evaluate the efficacy of the inventive compositions for the treatment of HSV-1 RE strain-induced corneal stromal infection.

Eighteen NZW rabbits were examined with a slit lamp after instillation of fluorescein to ascertain the presence of pre-existing corneal defects. All the animals were then bilaterally inoculated with $10^5$ PFU RE strain HSV-1. On day 3 post-inoculation, all of the eyes were examined and graded by slit lamp biomicroscopy. The animals were divided into three groups with matched corneal and stromal involvement (3 groups of 6 animals each). Dosages were given 9 times per day, 1 drop in each eye. Treatment was with Compound 23 (1 mg/ml), 1% trifluorothymidine, and placebo. The treatment was continued for seven days. The animals were observed by slit lamp examinations daily to evaluate efficacy of the treatments. Tear film cultures were performed on days 3, 5, and 7 post-inoculation.

Moderate to severe stromal disease in all rabbits was observed by the third day after inoculation. The average stromal disease score was 2.75+ or 60–70% of the corneal stroma. The range of severity was from 0.5–4.0+. The following observations were made on day 7 post-inoculation:

a) 12 out of 12 placebo-treated eyes had stromal disease ranging from 3.0–4.0+ (75–100% stromal involvement).

b) 12 out of 12 TFT-treated eyes had stromal disease ranging from 2.75–4.0+ (65–100% stromal involvement).

c) 9 out of 12 eyes treated with Compound 23 had stromal disease ranging from 2.75–4.0+; 3 out of the 12 eyes had stromal involvement ranging from 0.5–1.25+ (15–40% involvement of the corneal stroma). The 3 out of 12 eyes which appeared to respond to therapy with Compound 23 had initial stromal severity scores of 0.75–1.5+.

FIG. 6 depicts the results of corneal stromal therapy for those animals (eyes) that had moderate to severe disease severity at the beginning of therapy. The results show that at this level of disease progression, neither TFT nor Compound 23 therapy was effective. It should be noted that patients rarely present with this clinical stage of the disease.

It is concluded that the placebo and TFT therapies produced a 100% failure rate, in that all of the eyes in these two groups demonstrated increasing stromal severity throughout the course of the treatment.

In contrast, only 9 out of 12 eyes treated with Compound 23 exhibited increased stromal disease during the course of treatment. The remaining 3 out of 12 eyes treated with Compound 23 improved during the course of therapy.

EXAMPLE 5

This example represents a repeat of Example 4 to evaluate efficacy of Compound 23 during mild to moderate stromal disease.

The same procedure as in Example 4 was utilized.

FIG. 5 shows that the epithelial disease scores in the placebo-treated eyes peaked on the 6th to 7th day post-inoculation. Epithelial disease scores peaked on day 6 post-inoculation for eyes treated with TFT and Compound 23.

Epithelial HSV disease for eyes treated with Compound 23 and TFT decreased on the second day after therapy. As stromal disease developed (with virus replication in the corneal stroma) epithelial disease in the Compound 23 and TFT groups increased on days 5 and 6 post therapy. The difference in epithelial disease was due to central epithelial geographic figures in both eyes of one rabbit. In general, these data indicate that therapy with Compound 23 and TFT are roughly comparable with respect to epithelial disease involvement in this model of corneal stromal infection.

FIG. 7 depicts the therapeutic results of this study observed in eyes with mild to moderate disease severity upon onset of therapy. These data indicate that TFT had little, if any, effect on the course of the disease. In contrast, Compound 23 delayed the progression of the disease and significantly reduced the disease severity. This is the most frequent stage of the disease which is observed clinically.

Table 5 shows the percent of eyes in which HSV virus was recovered from tear film cultures. Table 6 shows the success and failure rates for eyes treated with Compound 23 and TFT.

TABLE 5

| | HSV TEAR FILM RECOVERY | | |
|---|---|---|---|
| | Days Post-inoculation | | |
| Therapy | 3 | 5 | 7 |
| Placebo | 100% | 100% | 80% |
| Compound 23 | 100% | 60% | 40% |
| TFT | 100% | 60% | 20% |

TABLE 6

| COMPARISON OF SUCCESS AND FAILURE RATES OF COMPOUND 23- AND TFT-TREATED EYES | | | | |
|---|---|---|---|---|
| | Success | No Change | Failure | No Disease |
| Compound 23 | 3/10 | 0/10 | 5/10* | 2/10** |
| TFT | 0/10 | 1/10 | 7/10 | 2/10 |

*Of the 5/10 eyes that failed to respond to Compound 23 therapy, 4/10 eyes had moderate stromal disease on the first day of Compound 23 therapy.
**1/10 eyes treated with the placebo failed to develop stromal disease. Accordingly, 1/10 eyes developed no stromal disease as a result of treatment with Compound 23 and this is considered to be therapy success.

Evaluation of the stromal disease in each of the treated groups is as follows:

Placebo

1/10 eyes exhibited no evidence of stromal disease on any post therapy day.

8/10 eyes had stromal disease involving >25% of the corneal stroma. The range of stromal disease was 25-90% of the corneal stroma.

1/10 eyes had stromal disease involving 10-15% of the corneal stroma.

Stromal disease involvement peaked on day 9 post-inoculation.

TFT

2/10 eyes exhibited no evidence of stromal disease on any day after therapy began.

4/10 eyes exhibited moderate stromal infection on the 3rd day after inoculation (30-70% involvement). These did not resolve by day 7 after inoculation (30-100% stromal involvement). This was considered a treatment failure.

1/10 eyes with mild stromal infection on the 3rd days after inoculation (15-20% initial involvement) did not resolve the stromal infection and had mild stromal disease on the 7th day after inoculation (10-15% stromal involvement). This was considered a partial or nominal therapy success.

3/10 eyes exhibited no corneal stromal disease by day 3 post-inoculation. These demonstrated stromal disease progression to a 40-50% involvement by the 7th day after inoculation. This was considered a treatment failure.

The stromal disease involvement in The TFT-treated animals peaked on day 9 post-inoculation.

Compound 23

2/10 eyes exhibited no evidence of stromal involvement on any day after therapy began.

4/10 eyes exhibited moderate stromal disease (1.5-3+ involvement; 35-75% stromal involvement) by day 3 post-inoculation. These did not resolve by day 7 after inoculation (50-75% stromal involvement). This was considered a treatment failure. 3/10 eyes with mild stromal disease involvement on the 3rd day after inoculation resolved by day 7 after inoculation (>5% corneal stromal involvement). This was considered a treatment success.

1/10 eyes with mild to no stromal involvement on the 3rd day after inoculation exhibited increasing stromal disease by day 7 after inoculation (50-60% corneal involvement). This was considered a treatment failure.

The stromal disease for eyes treated with Compound 23 peaked on day 6 post-inoculation.

From this study, it was concluded that compound 23 therapy altered the normal course of stromal disease when therapy was initiated during zero to mild stromal disease (0-15% initial corneal stromal involvement). TFT was ineffective in preventing the development of stromal disease. The difference in the time to achieve peak stromal disease development in Compound 23-treated (day 6 post-infection) compared to the TFT-treated eyes (i.e., day 9 post-infection) represents a significant and positive alteration in clinical course in favor of Compound 23 therapy versus TFT therapy.

What is claimed is:

1. An antiviral composition comprising a suitable carrier and a compound in anti-herpesvirus effective amount, the compound having the structure

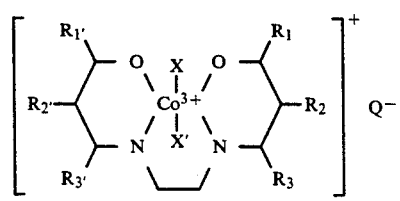

wherein $R_1$ and $R_1$, are the same or different and each is an alkyl group, a phenyl group or a substituted derivative of a phenyl group;

wherein $R_2$ and $R_2$, are the same or different and each is hydrogen, an unbranched alkyl group, a halide or a group having the structure

wherein R is hydrogen, an alkoxide group, an alkyl group, or OH;

wherein $R_3$ and $R_3$, are the same or different and each is hydrogen or an alkyl group;

wherein X and X' are the same or different and each is a water soluble group having weak to intermediate ligand field strength; and $Q^-$ is a soluble, pharmaceutically acceptable negative ion.

2. An antiviral composition comprising a suitable carrier and a compound in an anti-adenovirus effective amount, the compound having the structure

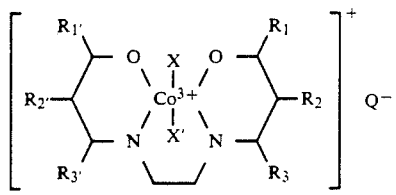

wherein $R_1$ and $R_1$, are the same or different and each is an alkyl group, a phenyl group or a substituted derivative of a phenyl group;

wherein $R_2$ and $R_2$, are the same or different and each is hydrogen, an unbranched alkyl group, a halide or a group having the structure

wherein R is hydrogen, an alkoxide group, an alkyl group, or OH;

wherein $R_3$ and $R_3$, are the same or different and each is hydrogen or an alkyl group;

wherein X and X' are the same or different and each is a water soluble group having weak to intermediate ligand field strength; and $Q^-$ is a soluble, pharmaceutically acceptable negative ion.

3. The composition of claim 1 wherein $R_1$ and $R_1$, are the same and each is a $C_1$-$C_5$ alkyl group, a phenyl group or a substituted derivative of a phenyl group where each substituent is a halide, an alkyl group or a group having the structure

where R is hydrogen, an alkoxide group, an alkyl group or OH; $R_2$ and $R_2$, are the same and each is a $C_1$-$C_3$ alkyl group, a halide, hydrogen, or a group having the structure

wherein R is H, $CH_3$ or OH; $R_3$ and $R_3$, are the same and each is a $C_1$-$C_3$ alkyl group; X and X, are the same and each is $NH_3$; and $Q^-$ is $Br^-$ or $Cl^-$.

4. The composition of claim 1 wherein the compound has a structure:

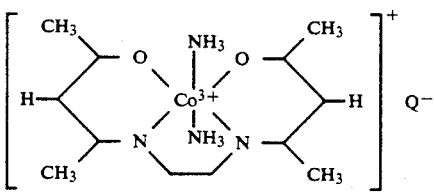

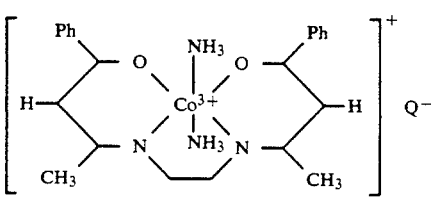

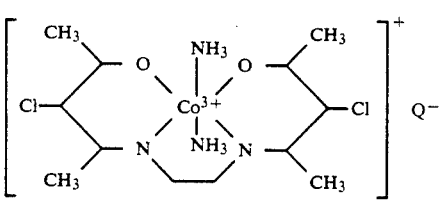

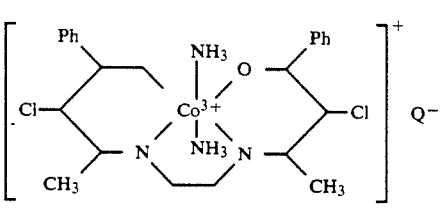

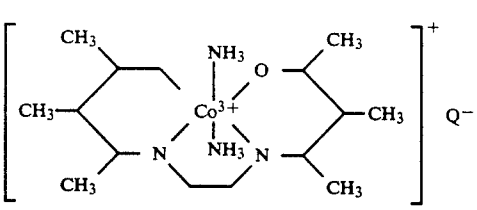

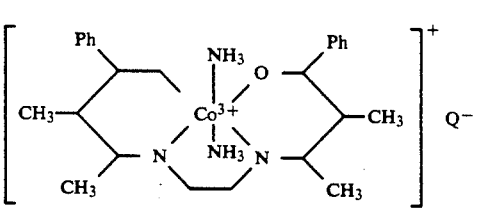

wherein Ph is a phenyl group.

5. The composition of claim 2 wherein $R_1$ and $R_1$, are the same and each is a $C_1$-$C_5$ alkyl group, a phenyl group or a substituted derivative of a phenyl group where each substituent is a halide, an alkyl group or a group having the structure

where R is hydrogen, an alkoxide group, an alkyl group or OH; $R_2$ and $R_2$, are the same and each is a $C_1$-$C_3$ alkyl group, a halide, hydrogen, or a group having the structure

wherein R is H, $CH_3$ or OH; $R_3$ and $R_3$, are the same and each is a $C_1$-$C_3$ alkyl group; X and X, are the same and each is $NH_3$; and $Q^-$ is $Br^-$ or $Cl^-$.

6. The composition of claim 3 wherein the compound has a structure:

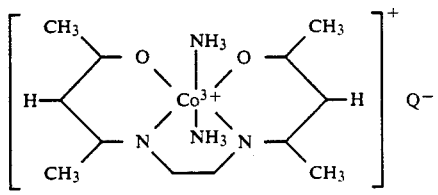

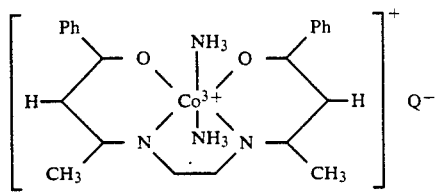

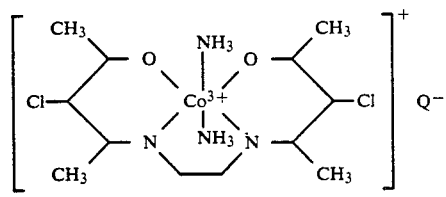

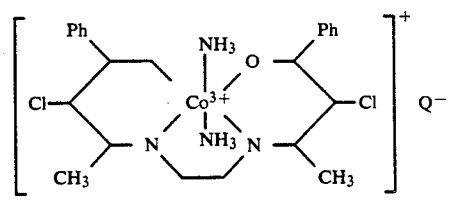

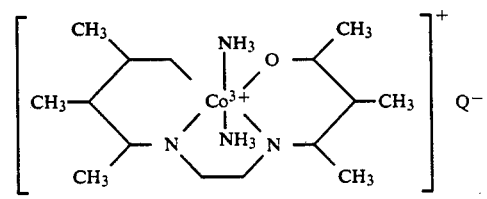

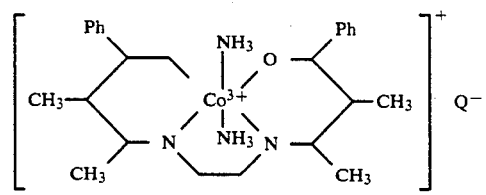

wherein Ph is a phenyl group.

7. The composition of claim 1 wherein the compound is present in an anti-HSV-1, HSV-2, HCMV, or VZV effective amount.

8. The composition of claim 3 wherein the compound is present in an anti-HSV-1, HSV-2, HCMV, or VZV effective amount.

9. The composition of claim 4 wherein the compound is present in an anti-HSV-1, HSV-2, HCMV, or VZV effective amount.

10. An antiviral composition comprising a pharmaceutically acceptable carrier and a complex in an anti-herpes effective amount, the complex comprising a Co(III) complex having an octahedral basal plane defined by four donor atoms A, which may be the same or different, and two axial ligand donor atoms B, which may be the same or different, said donor atoms having a ligand field strength equal to or less than $CN^-$, said complex reacting with $O_2^-$ to form a Co(III)-$O_2$ adduct or oxidizing $O_2^-$ to produce dioxygen and a Co(II) complex.

11. The composition of claim 10 wherein the complex has a quadridentate ligand L bound to the Co(III) through the donor atoms which imposes planarity on the octahedral basal plane.

12. The composition of claim 11 wherein the quadridentate ligand L and bonded Co(III) comprises a 6, 5, 6 ring system, said 6-membered ring of said 6, 5, 6 ring system being unsaturated.

13. The composition of claim 12 wherein the complex has the formula $[CoL(B)_2]^n$ wherein B is selected from the group consisting of $I^-$, $Br^-$, $Cl^-$, $F^-$, $OH^-$, $C_2O_4^{2-}$, $H_2O$, and $NH_3$; and n is $-1$, 0, or $+1$.

14. An antiviral composition comprising a pharmaceutically acceptable carrier and a complex in an anti-adenovirus effective amount comprising a Co(III) complex having an octahedral basal plane defined by four donor atoms A, which may be the same or different, and two axial ligand donor atoms B, which may be the same or different, said donor atoms having a ligand field strength equal to or less than $CN^-$, said complex reacting with $O_2^-$ to form a Co(III)-$O_2$ adduct or oxidizing $O_2^-$ to produce dioxygen and a Co(II) complex.

15. The composition of claim 14 wherein the complex has a quadridentate ligand L bound to the Co(III) through the donor atoms which imposes planarity on the octahedral basal plane.

16. The composition of claim 15 wherein the quadridentate ligand L and bonded Co(III) comprises a 6, 5, 6 ring system, said 6-membered ring of said 6, 5, 6 ring system being unsaturated.

17. The composition of claim 16 wherein the complex has the formula $[CoL(B)_2]^n$ wherein B is selected from the group consisting of $I^-$, $Br^-$, $Cl^-$, $F^-$, $OH^-$, $C_2O_4^{2-}$, $H_2O$, and $NH_3$; and n is $-1$, 0, or $+1$.

18. In a method for treating a subject having a disease caused by a herpes virus wherein a composition containing a pharmaceutically acceptable carrier and a compound which is administered to the subject in an anti-herpesvirus effective amount, the improvement which comprises said composition being the composition of claim 1.

19. In a method for treating a subject having a disease caused by an adenovirus wherein a composition containing a pharmaceutically acceptable carrier and a compound which is administered to the subject in an anti-adenovirus effective amount, the improvement which comprises said composition being the composition of claim 2.

20. In the method for treating a subject having a disease caused by a herpes virus wherein a composition containing a pharmaceutically acceptable carrier and a compound which is administered to the subject in an anti-herpesvirus effective amount, the improvement which comprises said composition being the composition of claim 3.

21. In the method for treating a subject having a disease caused by a herpes virus wherein a composition containing a pharmaceutically acceptable carrier and a compound which is administered to the subject in an anti-herpesvirus effective amount, the improvement which comprises said composition being the composition of claim 4.

22. In a method for treating a subject having a disease caused by an adenovirus wherein a composition containing a pharmaceutically acceptable carrier and a compound which is administered to the subject in an anti-adenovirus effective amount, the improvement which comprises said composition being the composition of claim 5.

23. In a method for treating a subject having a disease caused by an adenovirus wherein a composition containing a pharmaceutically acceptable carrier and a compound which is administered to the subject in an anti-adenovirus effective amount, the improvement which comprises said composition being the composition of claim 6.

24. In the method for treating a subject having a disease caused by a herpes virus wherein a composition containing a pharmaceutically acceptable carrier and a compound which is administered to the subject in an anti-herpesvirus effective amount, the improvement which comprises said composition being the composition of claim 7.

25. In the method for treating a subject having a disease caused by a herpes virus wherein a composition containing a pharmaceutically acceptable carrier and a compound which is administered to the subject in an anti-herpesvirus effective amount, the improvement which comprises said composition being the composition of claim 8.

26. In the method for treating a subject having a disease caused by a herpes virus wherein a composition containing a pharmaceutically acceptable carrier and a compound which is administered to the subject in an anti-herpesvirus effective amount, the improvement which comprises said composition being the composition of claim 9.

27. In the method for treating a subject having a disease caused by a herpes virus wherein a composition containing a pharmaceutically acceptable carrier and a compound which is administered to the subject in an anti-herpesvirus effective amount, the improvement which comprises said composition being the composition of claim 10.

28. In the method for treating a subject having a disease caused by a herpes virus wherein a composition containing a pharmaceutically acceptable carrier and a compound which is administered to the subject in an anti-herpesvirus effective amount, the improvement which comprises said composition being the composition of claim 11.

29. In the method for treating a subject having a disease caused by a herpes virus wherein a composition containing a pharmaceutically acceptable carrier and a compound which is administered to the subject in an anti-herpesvirus effective amount, the improvement which comprises said composition being the composition of claim 12.

30. In the method for treating a subject having a disease caused by a herpes virus wherein a composition containing a pharmaceutically acceptable carrier and a compound which is administered to the subject in an anti-herpesvirus effective amount, the improvement which comprises said composition being the composition of claim 13.

31. In a method for treating a subject having a disease caused by an adenovirus wherein a composition containing a pharmaceutically acceptable carrier and a compound which is administered to the subject in an anti-adenovirus effective amount, the improvement which comprises said composition being the composition of claim 14.

32. In a method for treating a subject having a disease caused by an adenovirus wherein a composition containing a pharmaceutically acceptable carrier and a compound which is administered to the subject in an anti-adenovirus effective amount, the improvement which comprises said composition being the composition of claim 15.

33. In a method for treating a subject having a disease caused by an adenovirus wherein a composition containing a pharmaceutically acceptable carrier and a compound which is administered to the subject in an anti-adenovirus effective amount, the improvement which comprises said composition being the composition of claim 16.

34. In a method for treating a subject having a disease caused by an adenovirus wherein a composition containing a pharmaceutically acceptable carrier and a compound which is administered to the subject in an anti-adenovirus effective amount, the improvement which comprises said composition being the composition of claim 17.

* * * * *